United States Patent
McGrogan et al.

(10) Patent No.: US 8,504,134 B2
(45) Date of Patent: Aug. 6, 2013

(54) LATERALLY FENESTRATED CANNULA

(75) Inventors: Anthony McGrogan, San Jose, CA (US); Paul Lilagan, Sunnyvale, CA (US); Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 487 days.

(21) Appl. No.: 12/571,675

(22) Filed: Oct. 1, 2009

(65) Prior Publication Data

US 2011/0082365 A1  Apr. 7, 2011

(51) Int. Cl.
*A61B 5/05* (2006.01)

(52) U.S. Cl.
USPC ............... 600/407; 600/424; 604/22; 604/48; 604/93.01; 604/264; 604/284; 606/108; 606/130; 606/191

(58) Field of Classification Search
USPC ........... 600/424; 606/130, 108, 191; 604/264, 604/284, 48, 22, 93.01
See application file for complete search history.

(56) References Cited

U.S. PATENT DOCUMENTS

| | | | |
|---|---|---|---|
| 5,002,557 A | | 3/1991 | Hasson |
| 5,183,471 A | | 2/1993 | Wilk |
| 5,251,611 A | | 10/1993 | Zehel et al. |
| 5,269,772 A | | 12/1993 | Wilk |
| 5,486,154 A | | 1/1996 | Kelleher |
| 5,505,210 A | * | 4/1996 | Clement ................... 600/566 |
| 5,669,883 A | | 9/1997 | Scarfone et al. |
| 5,748,767 A | | 5/1998 | Raab |
| 6,203,554 B1 | * | 3/2001 | Roberts .................... 606/144 |
| 6,468,203 B2 | | 10/2002 | Belson |
| 6,522,906 B1 | * | 2/2003 | Salisbury et al. ........... 600/407 |
| 6,712,773 B1 | * | 3/2004 | Viola ........................ 600/564 |
| 6,984,203 B2 | | 1/2006 | Tartaglia et al. |
| 7,338,473 B2 | | 3/2008 | Campbell et al. |
| 2008/0065103 A1 | * | 3/2008 | Cooper et al. .............. 606/130 |
| 2009/0023985 A1 | | 1/2009 | Ewers |
| 2011/0040404 A1 | | 2/2011 | Diolaiti et al. |

* cited by examiner

*Primary Examiner* — James Kish

(57) ABSTRACT

A cannula provides access to a surgical site for a camera instrument and one or more minimally invasive surgical instruments. The cannula may include a curved or flexible section when used with flexible surgical instruments. A service port is defined in a sidewall between proximal and distal ends of the cannula, the service port being large enough to allow an object to be transferred between the instruments and a location outside the cannula. An end effector of the surgical instrument may be positioned within the cannula adjacent the service port. The camera instrument may be positioned to place the end effector within a field of view of the camera. An object may be transferred between a service instrument and the surgical instrument within the field of view of the camera.

21 Claims, 7 Drawing Sheets

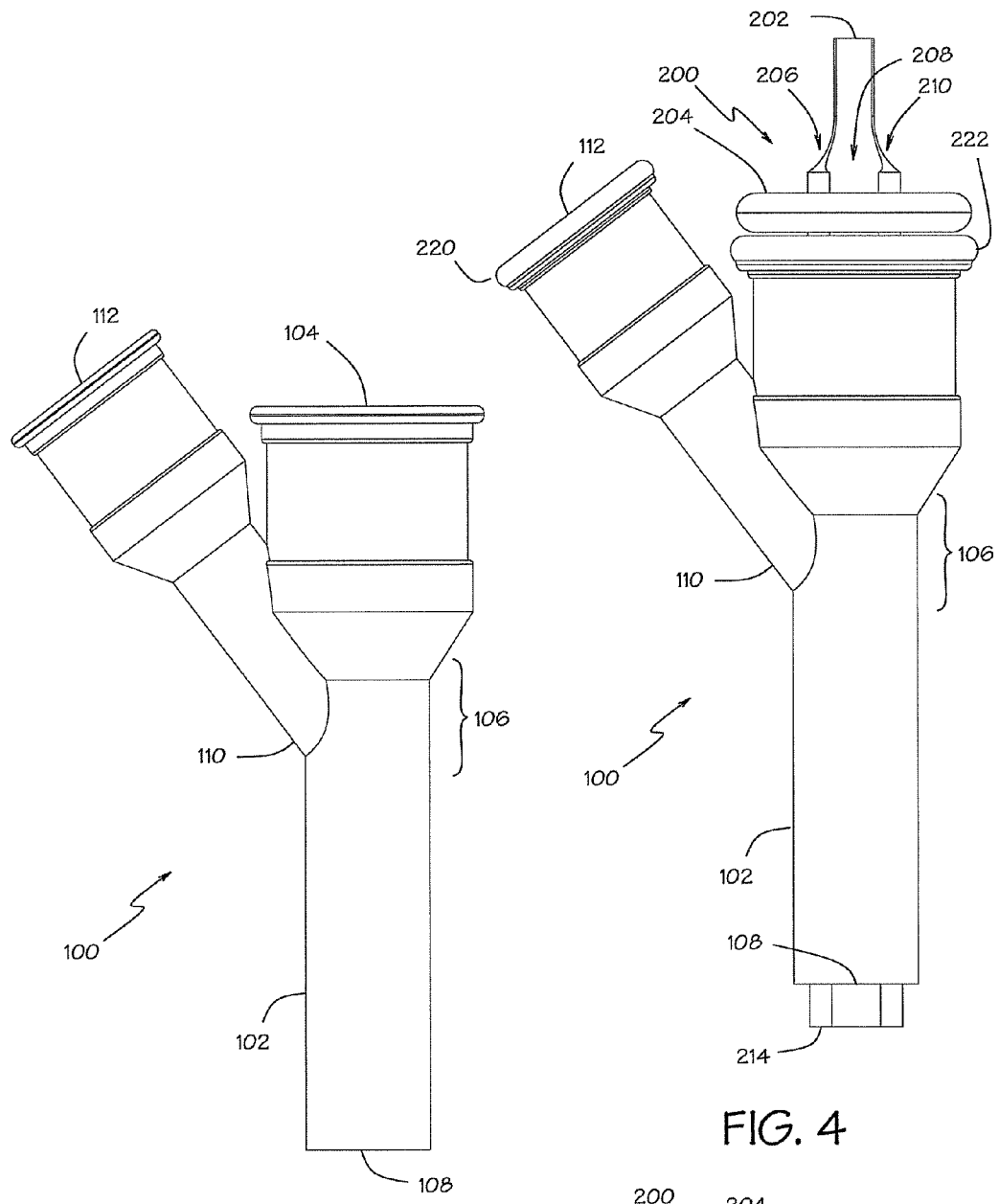
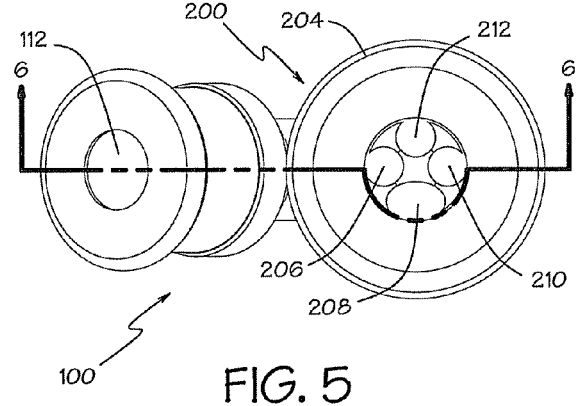
FIG. 3
FIG. 4
FIG. 5

LATERALLY FENESTRATED CANNULA

BACKGROUND

1. Field

This invention relates to cannulas of the type used to perform minimally invasive surgery and, more particularly, to cannulas that allow a minimally invasive surgical instrument to be serviced without being removed from the cannula.

2. Background

Minimally invasive surgery (MIS) (e.g., endoscopy, laparoscopy, thoracoscopy, cystoscopy, and the like) allows a patient to be operated upon through small incisions by using a camera and elongated surgical instruments introduced to an internal surgical site. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

One or more cannulas may be passed through small (generally 1 inch or less) incisions or a natural body orifice to provide entry ports for the minimally invasive (e.g., endoscopic, laparoscopic, and the like) surgical instruments, including a camera instrument (e.g., endoscope, laparoscope, and the like). A surgeon is able to perform surgery by manipulating the surgical instruments externally to the surgical site under the view provided by the camera instrument.

Manipulating minimally invasive surgical instruments may be more difficult than using conventional surgical instruments in open surgery because of the need to manipulate the instruments by means of the elongate shafts, which are constrained in their movement by the need to avoid translation of the instrument where it enters the patient. Robotic surgery allows minimally invasive surgical instruments to be manipulated by servo controllers that the surgeon controls from a remote console. The use of servo controllers and robotic surgery allows more precise and intuitive control of the surgical instruments and simplifies for the surgeon the considerations of the motion constraints on the surgical instruments.

It is typical to provide several cannulas for a minimally invasive surgical procedure. Generally each cannula will provide access to the surgical site for a single surgical or camera instrument. For example, four cannulas may be provided with one cannula being used to introduce a camera instrument and the remaining three cannulas being used to introduce surgical instruments. While the small incisions necessary for placing a cannula are less traumatic than the incision necessary for open surgery, each incision still represents a trauma to the patient.

In an effort to reduce the trauma of minimally invasive surgery even further, techniques are being developed to allow minimally invasive surgery using only a single cannula. This may be accomplished by using a somewhat larger cannula that can accommodate all of the instruments required for the surgery. Minimally invasive surgery performed through a single cannula may be referred to as single port access (SPA) surgery. The single cannula may be introduced through a body orifice and be referred to as Natural Orifice Transdermal Endoscopic Surgery (NOTES). Single port surgery may also be referred to as bellybutton surgery when the navel (umbilicus) is used as the location for the single cannula.

Minimally invasive single port surgery may in some instances be more difficult and time-consuming than minimally invasive surgery using multiple entry ports. One aspect that may increase the time required when using a single cannula for all instruments is the difficulty of inserting a surgical instrument into the cannula because of the lack of space around the cannula where multiple instruments are located. During the course of a surgical procedure, it may be necessary to remove and reinsert a surgical instrument multiple times in order to service the instrument in various ways. For example, it may be necessary to remove and reinsert an instrument to remove an object, such as a sponge or specimen, from the surgical site. As another example, it may be necessary to remove and reinsert an instrument to supply a clamp or a suture to the surgical site. As yet another example, it may be necessary to remove and reinsert an instrument to clean the instrument, such as cleaning the lens or illumination port on a camera instrument. Removing and re-inserting surgical instruments may consume a substantial amount of time and disrupt the progress and workflow of the surgical procedure. The time and disruption created by removing and re-inserting surgical instruments may be greater when the instruments are controlled by robotic actuators because the actuators further crowd the space around the cannula.

In view of the above, it would be desirable to provide an improved apparatus and method for carrying out minimally invasive surgical procedures that reduces the need for removing and reinserting surgical instruments and/or camera instruments into the cannula.

SUMMARY

A cannula includes a tubular member that provides access to a surgical site for two or more minimally invasive surgical instruments, which may include a camera. A service port is coupled to the tubular member adjacent a central region of the tubular member and external to the surgical site. A surgical instrument may grasp an object and move it to the central region. A retrieving instrument introduced through the service port may take the object from the surgical instrument and remove it from the cannula so that the surgical instrument is not removed from the cannula. The cannula may include a slidable guide that supports the surgical instruments. The cannula may include a flexible section and may be used with flexible surgical instruments. The guide may be slid away from the central region before removing an object. The camera may be withdrawn into the cannula to observe the transfer.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 3 is a side view of a cannula for use in minimally invasive surgery.

FIG. 4 is a side view of the cannula of FIG. 3 with additional elements that may be used with the cannula.

FIG. 5 is a top view of the cannula and additional elements of FIG. 4.

DETAILED DESCRIPTION

In the following description, numerous specific details are set forth. However, it is understood that embodiments of the invention may be practiced without these specific details. In other instances, well-known devices, structures, and techniques have not been shown in detail in order not to obscure the understanding of this description. The term "flexible" in association with a mechanical structure or component should be broadly construed. In essence, it means the structure or component can be bent without harm. For example, a flexible mechanical structure may include a series of closely spaced components that are similar to "vertebrae" in a snake-like arrangement. In such an arrangement, each component is a short link in a kinematic chain, and movable mechanical constraints (e.g., pin hinge, cup and ball, and the like) between each link may allow one (e.g., pitch) or two (e.g., pitch and yaw) degrees of freedom (DOF) of relative movement between the links. As another example, a flexible mechanical structure may be continuous, such as a closed bendable tube (e.g., nitinol, polymer, and the like) or other bendable piece (e.g., kerf-cut tube, helical coil, and the like). Accordingly, a short, flexible structure may serve as, and be modeled as, a single mechanical constraint (joint) providing one or more DOFs between two links in a kinematic chain, even though the structure itself may be a kinematic chain made of several coupled links.

Figure 1:
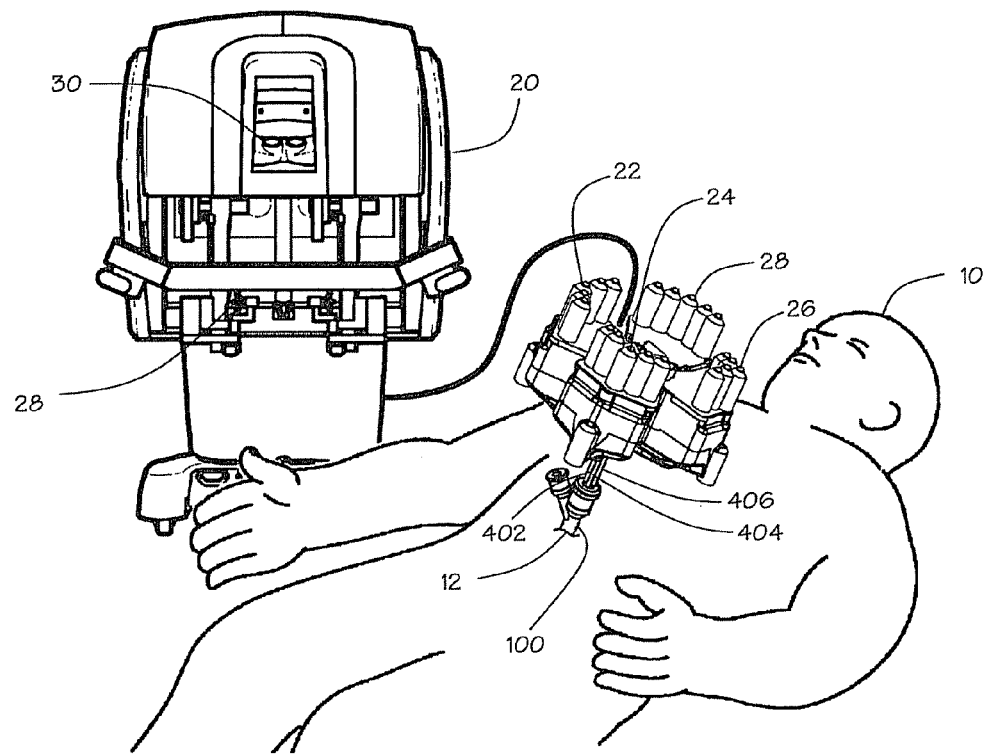
FIG. 1 is a pictorial view of a minimally invasive surgery using single port access for two robotic surgical instruments.

FIG. 1 shows a pictorial view of a minimally invasive surgery on a patient 10 using single port access 12 for four robotic surgical instruments 402, 404, 406, where the fourth instrument is hidden behind the other three instruments. Typically three or four surgical instruments, including a camera instrument, would be introduced through the access port 12. In addition, there will generally be provisions for introducing an insufflation gas, such as carbon dioxide ($CO_2$), at or near the access port. It will be appreciated that single port surgery requires a substantial amount of equipment to be located in a small amount of space.

Figure 2:
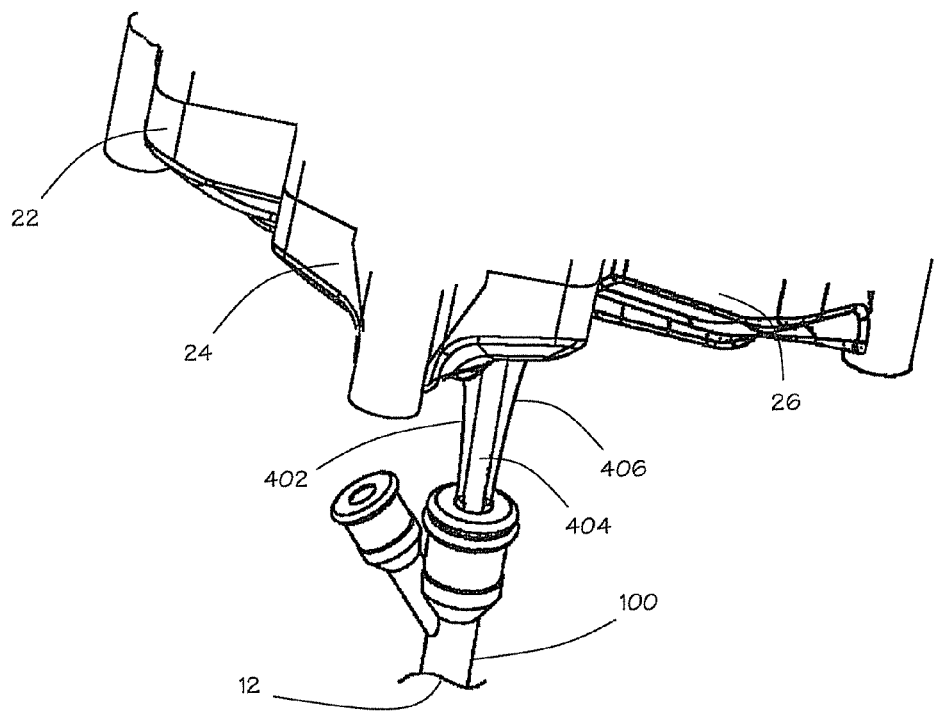
FIG. 2 is a pictorial view of the two robotic surgical instruments and a cannula providing the single port access shown in FIG. 1.

FIG. 2 shows a pictorial view of three of the robotic surgical instruments 402, 404, 406 and a cannula 100 providing the single port access shown in FIG. 1. The robotic surgical instruments 402, 404, 406 which may include a camera instrument that may provide images of the surgical site and other instruments, are coupled to actuators 22, 24, 26, such as servo actuators that allow a surgeon to manipulate the surgical instruments using a computer mediated control station 20 (FIG. 1). These manipulations may include functions such as positioning, grasping, and moving. Such actuator control of surgical instruments may be referred to as robotic surgery.

Referring again to FIG. 1, the computer mediated control station 20 may provide hand operated controllers 28 that allow manipulation of the robotic surgical instruments 402, 404, 406 by transmitting signals, such as electrical control signals provided by cables 22, to the actuators 22, 24, 26, 28 that control the actions of the coupled surgical instruments 402, 404, 406. Typically one of the surgical instruments 404 will be a camera instrument that is manipulated to place the remaining surgical instruments and the objects being manipulated within a field of view of the camera. The camera instrument transmits signals to the control station 20 so that an image captured by the camera of the instruments and objects within the field of view can be displayed on a visual display 30 that viewed by the surgeon as the coupled surgical instruments 402, 404, 406 are manipulated. The hand operated controllers 28 and the visual display 30 may be arranged to provide an intuitive control of the surgical instruments 402, 404, 406, wherein the instruments respond in an expected manner to movements of the controllers.

The robotic servo actuators 22, 24, 26, 28 may provide a number of independent motions, perhaps eight independent motions, that control each surgical instrument. In particular, the robotic servo actuators 22, 24, 26, 28 allow the surgical instruments 402, 404, 406 to be positioned at various depths within the cannula 100 and beyond a distal end of the cannula within a surgical site. The robotic servo actuators 22, 24, 26, 28 may or may not allow the surgical instruments 402, 404, 406 to be withdrawn entirely from the cannula 100. In some embodiments, the surgical instruments 402, 404, 406 may be positioned at some depth into the cannula when the robotic servo actuators 22, 24, 26, 28 are at the limit of their retraction and complete removal of the instruments may require the actuators to be manually repositioned. As suggested by the figures, a robotic servo actuator is relatively bulky. Having three or four actuators coupled to instruments using a single access port 12 may require careful positioning of the actuators to accommodate all the actuators in the confined space around the single access port.

FIG. 3 shows a side view of the cannula 100 shown in FIGS. 1 and 2 for use in minimally invasive surgery with single port access. The cannula 100 includes a tubular member 102 that includes a proximal opening 104 spaced apart from a distal opening 108 by a central region 106. The proximal opening 104 is joined to the distal opening 108 by a sidewall that surrounds the central region 106. The distal opening 108 provides the only opening in the cannula 100 that is to be placed inside the patient. The proximal opening 104 is to be placed external to the patient to receive minimally invasive surgical instruments, including, e.g., a camera instrument that can image the surgical site. A service port 110 is defined in the sidewall adjacent the central region 106. The service port 110 provides a second opening 112 external to the patient. The service port 110 is sized to allow a transfer of an object between surgical instruments that are inside the cannula and a position outside the cannula. The service port 110 may receive service instruments that are used to service the surgical instruments introduced through the proximal opening 104 inside the cannula.

FIG. 4 shows a side view of the cannula 100 with additional elements that may be used with the cannula. Pressure seals 220, 222 may be placed over the second opening 112 and the proximal opening 104 to retain a pressurized insufflation gas (if used) within the body cavity. The pressure seals are shown as illustrative simple diaphragms with openings to allow instruments to pass through the seals. It will be appreciated that other forms of seals (e.g., air barrier) may be used to retain the pressurized insufflation gas within the body cavity while accommodating instruments passing through the seals and removing instruments from the cannula. The seals may further include arrangements that allow larger objects to be transferred to and from the cannula 100 while retaining the pressurized insufflation gas. It may be particularly advantageous to provide a sealing arrangement that permits the transfer of larger objects through the second opening 112.

FIG. 4 further shows an instrument guide 200 inserted through the tubular member 102 from the proximal opening 104 through the distal opening 108. The instrument guide 200 has a proximal end 202, a distal end 214, and at least two passages 206, 208, 210 from the proximal end to the distal end for slidably supporting surgical instruments. The instrument guide 200 is slidably located within the first tubular member 102. The instrument guide 200 may further include a grip structure 204 that may provide a convenient place to hold the instrument guide for positioning and may provide a stop that may rest against the proximal opening 104 to define the maximum insertion of the instrument guide into the cannula 100.

FIG. 5 shows a top view of the cannula 100 with the instrument guide 200 and the pressure seals 220, 222. As can be seen in this view, the exemplary instrument guide 200 illustrated includes four passages 206, 208, 210, 212. Thus the exemplary cannula 100 and instrument guide 200 illustrated allows up to four minimally invasive surgical instruments to be passed through a single cannula, which may minimize the number of incisions and attendant patient trauma for a surgery. As shown, one or more of the passages 208 may be of a size and/or shape to slidably support particular instruments, such as a camera instrument. In other embodiments, the instrument guide may have other arrangements of the plurality of passages to slidably support a particular group of instruments.

Figure 6A:
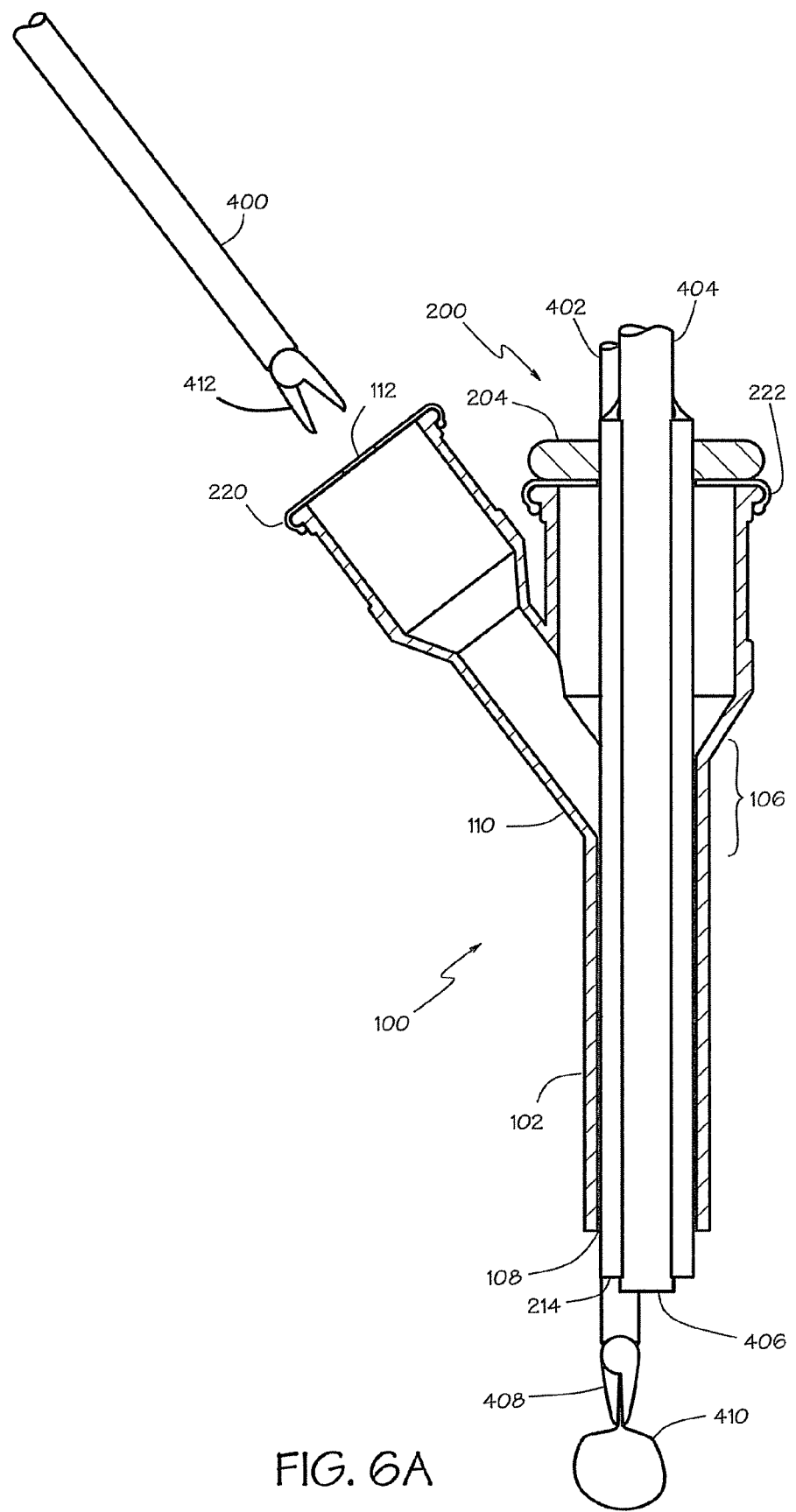
FIGS. 6A through 6C are cross-section views taken along the line 6-6 in FIG. 5 showing a method for removing an object from a surgical site with a minimally invasive surgical instrument.
Figure 6B:
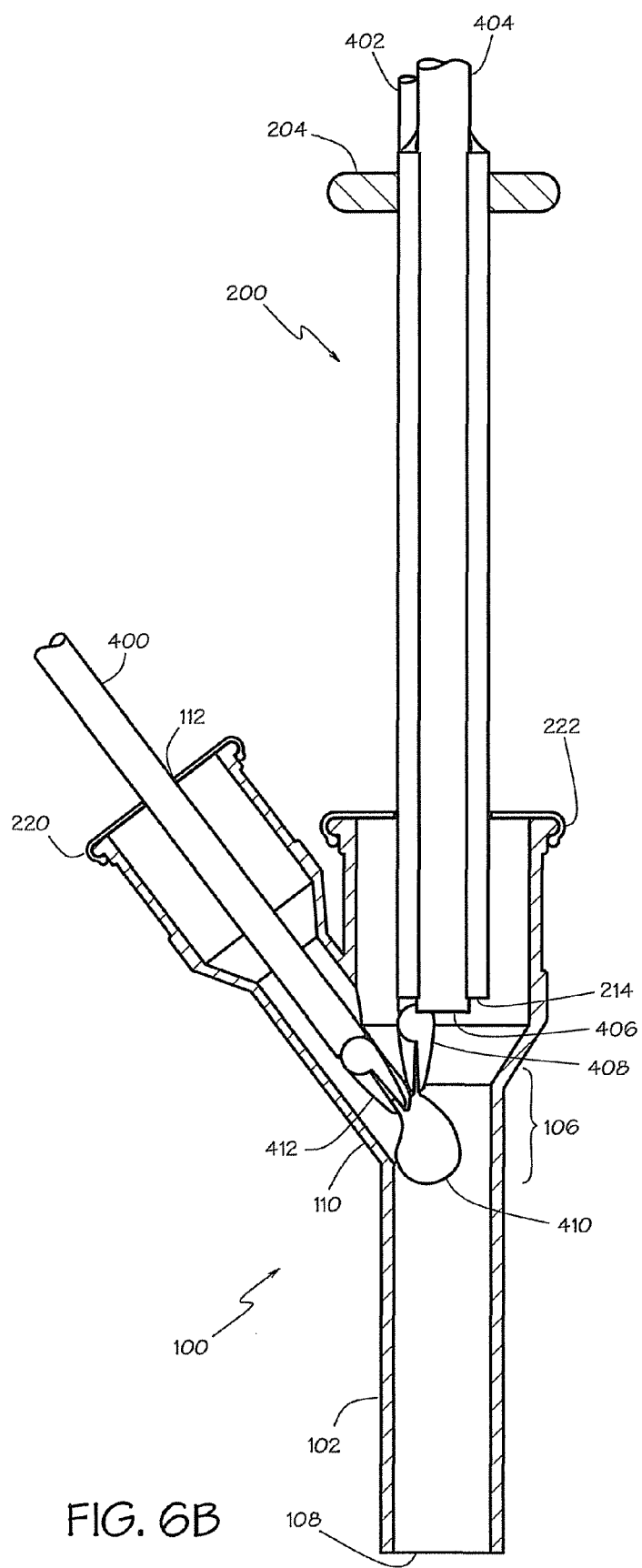
Figure 6C:
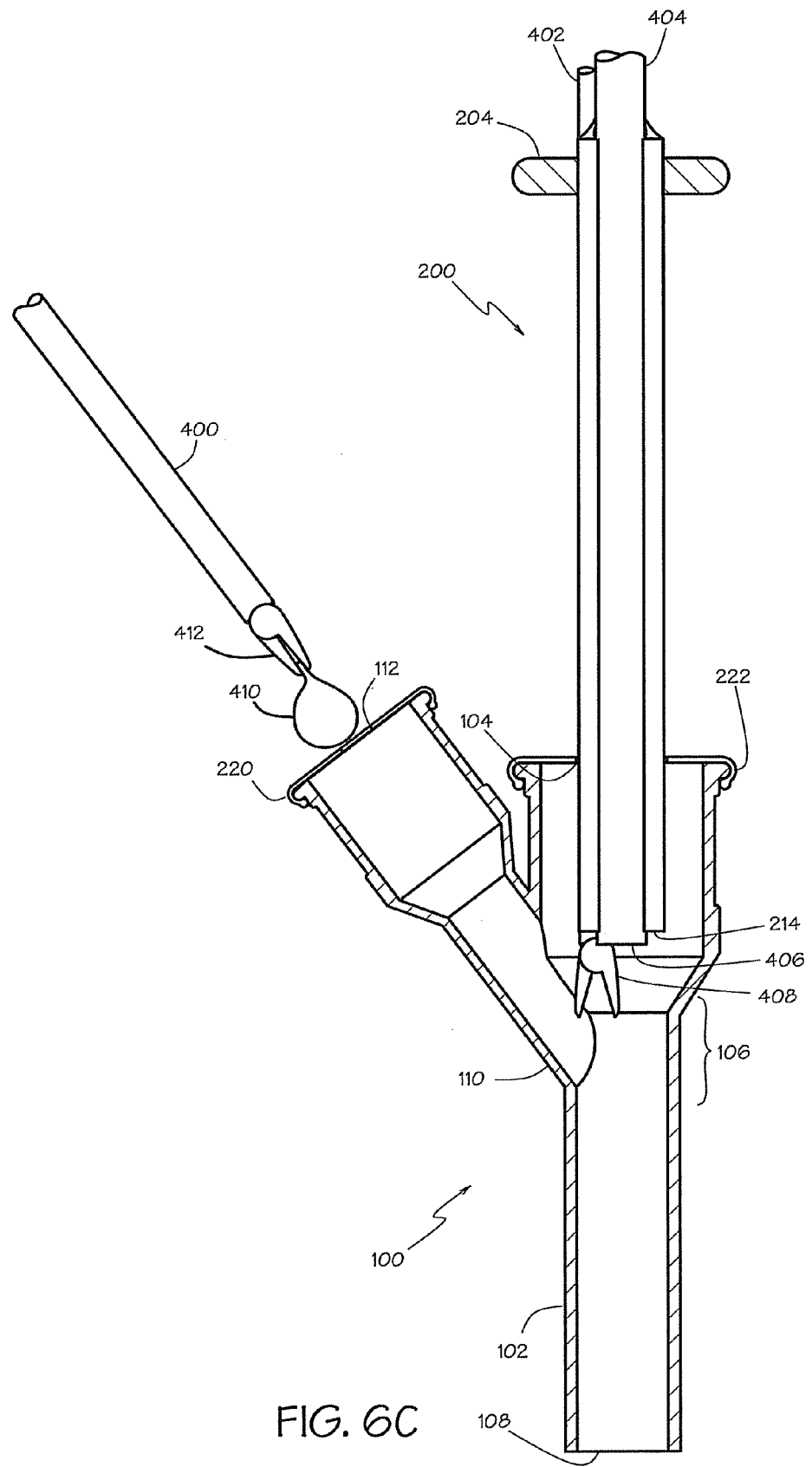

FIGS. 6A through 6C are cross-section views taken along the line 6-6 in FIG. 5. These figures show a method for removing an object from a surgical site with a minimally invasive surgical instrument. The method uses a cannula 100 of the type described above and shown in FIGS. 3-5.

Referring to FIG. 6A, a minimally invasive surgical instrument 402 enters the cannula 100 through the proximal opening 104. An endoscopic camera instrument 404 also enters the cannula 100 through the proximal opening 104. The surgical instrument 402 passes through the tubular member 102 to grasp an object 410 adjacent the distal opening 108 of the tubular member with an end effector 408, such as a forceps, at a distal end of the surgical instrument. The endoscopic camera instrument 404 provides an image from an imaging end 406 that is at a distal end of the camera instrument to allow the object 410 and the end effector 408 to be visualized during the grasping of the object with the surgical instrument 402.

Referring to FIG. 6B, the object 410 is moved from the distal opening 108 of the tubular member 102 into the central region 106 of the tubular member. The object 410 is moved by withdrawing the surgical instrument 402 into the cannula 100 thus positioning the end effector 408 of the surgical instrument within the cannula and adjacent the service port 110 defined in the sidewall of the cannula. The positioning may be accomplished by moving the surgical instrument 402 with the robotic servo actuator 24. The service port 110 is sized to allow transfer of the object 410 between the end effector 408 and a position outside the cannula 100.

The camera instrument 404 is also withdrawn into the cannula 100 and the camera instrument positioned to place the end effector 408, when positioned adjacent the service port 110, within a field of view of the camera instrument. This camera positioning allows visualization of the object 410 and the end effector 408 during subsequent portions of the process, such as displaying an image captured by the camera of the transfer of the object. The positioning may be accomplished by moving the camera instrument 404 with the robotic servo actuator 26.

When the exemplary instrument guide 200 shown in the figures is fully inserted into the cannula 100 such that the proximal end 202 of the instrument guide is adjacent the proximal opening 104 of the tubular member, the distal end 214 of the instrument guide may extend beyond the central region 106 of the tubular member. The instrument guide 200 may also be partially withdrawn into the cannula 100 before, after, or concurrently with the movement of the surgical instrument 402 such that distal end 214 of the guide is between the central region 106 and the proximal opening 104, above the end effector 408 and the grasped object 410, and out of the line of sight from the image forming end 406 to the end effector and/or the grasped object. Partially withdrawing the instrument guide may allow a better visualization of the end effector 408 and the grasped object 410 by the camera instrument 404. It is significant that the end effector 408 of the surgical instrument 402 remains in the cannula 100 and need not be removed.

A retrieving instrument 400 is introduced through second opening 112 and the service port 110 of the cannula 100. An end effector 412, such as a forceps, at the distal end of the retrieving instrument 400 is positioned in the central region 106 of the cannula 100, adjacent the end effector 408 of the surgical instrument 402 and the grasped object 410. The object is transferred from the surgical instrument 402 to the retrieving instrument 400 within the central region 106 of the tubular member 102.

The transfer of the object 410 may be performed under the visualization provided by the camera instrument 404. The image forming end 406 of the camera instrument 404 may be moved from the distal opening 108 of the tubular member 102 to a position within the tubular member such that the camera provides an image of the central region 106 of the tubular member before introducing the retrieving instrument 400 through the service port 110. In this way the object 410 is transferred from one instrument to the other without removing the surgical instrument used at the surgical site from the cannula and while a surgeon views and controls one or both instruments during the transfer to speed the transfer and the return of the surgical instruments to the surgical site. It is desirable that the exchange be done under direct view, and the camera provides that view for the surgeon.

Referring to FIG. 6C, the object 410 is removed from the cannula 100 by withdrawing the retrieving instrument 400 and the object from the service port 110 through the second opening 112 without removing the surgical instrument 402 from the cannula. This may allow the surgical instrument 402 to be returned to the surgical site more quickly and with less risk of contamination than would be the case if the surgical instrument was fully withdrawn from the cannula to remove the object 410 without the use of the second opening 112 and the service port 110 to provide access for a retrieving instrument 400.

Figures 7, 8:
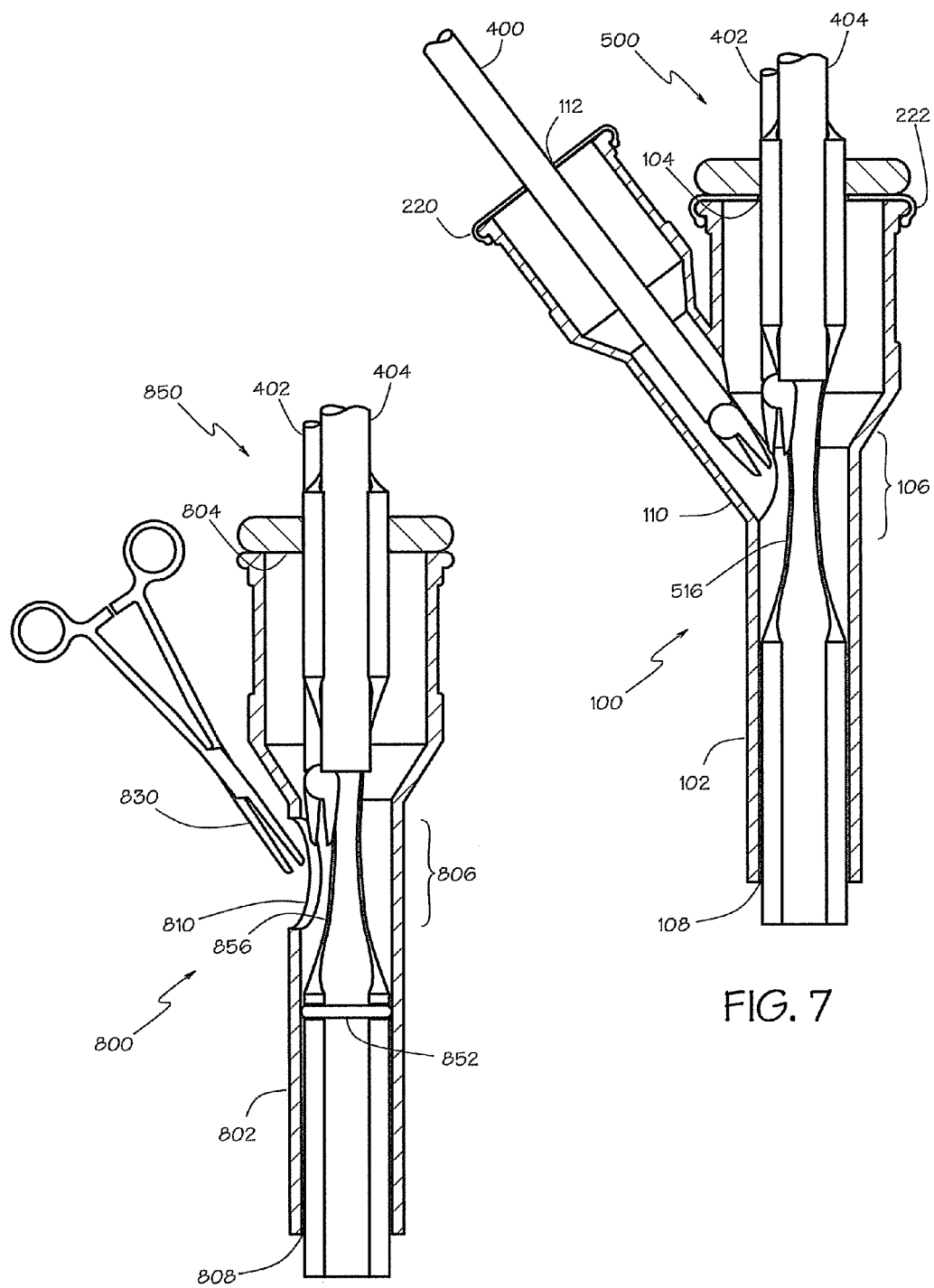
FIG. 7 is cross-section view of another embodiment taken along a line corresponding to the line 6-6 in FIG. 5.
FIG. 8 is cross-section view of yet another embodiment taken along a line corresponding to the line 6-6 in FIG. 5.

FIG. 7 is a cross-section view of another embodiment of an instrument guide 500 inserted through the tubular member 102 from the proximal opening 104 through the distal opening 108. In this embodiment, the instrument guide 500 includes a cut-away section 516 that is in the central portion 106 of the tubular member 102 when the instrument guide is fully inserted into the cannula 100. This may allow the ends of the surgical instruments 402, 404 to be withdrawn into the central portion 106 of the tubular member 102 and to be serviced by a servicing instrument 400 inserted into the central portion from the service port 110 without withdrawing the instrument guide 500.

FIG. 8 shows a cross-section view of another embodiment of a cannula 800 that includes a service port 810 in a sidewall 802 adjacent a central region 806. In this embodiment there is no extension from the service port 810. This may allow a conventional surgical instrument 830, such as forceps, hemostats, and the like, to be used as servicing instruments. A seal (not shown) may be provided on the service port 810 to retain insufflation gas within the surgical site. In the embodiment shown, a seal 852 is provided on the instrument guide 850 that provides a seal between the service port 810 and the distal end 808 of the cannula 800. In other embodiments, a seal (not shown) may be provided in the cannula between service port 810 and the distal end 808 of the cannula 800. In some cases, the service port 810 without extension may provide a direct line of sight to the central region 806 of the cannula and allow transfers to be made without using the camera instrument to provide a view of the transfer.

In the effort to reach the surgical site through a natural body orifice such as transoral, transvaginal, transanal or transumbilical, the tubular portion of the cannula may be curved or may have a flexible section. Surgical instruments having a flexible shaft may be inserted through such a cannula to perform surgery at the surgical site. The shaft of the surgical instruments would be sufficiently flexible to conform to the curve of the cannula as the instrument is passed from the proximal to the distal end of the cannula. Flexible surgical instrument may be standard endoscopic instrument for manual operation or robotically actuated instruments.

Figure 9:
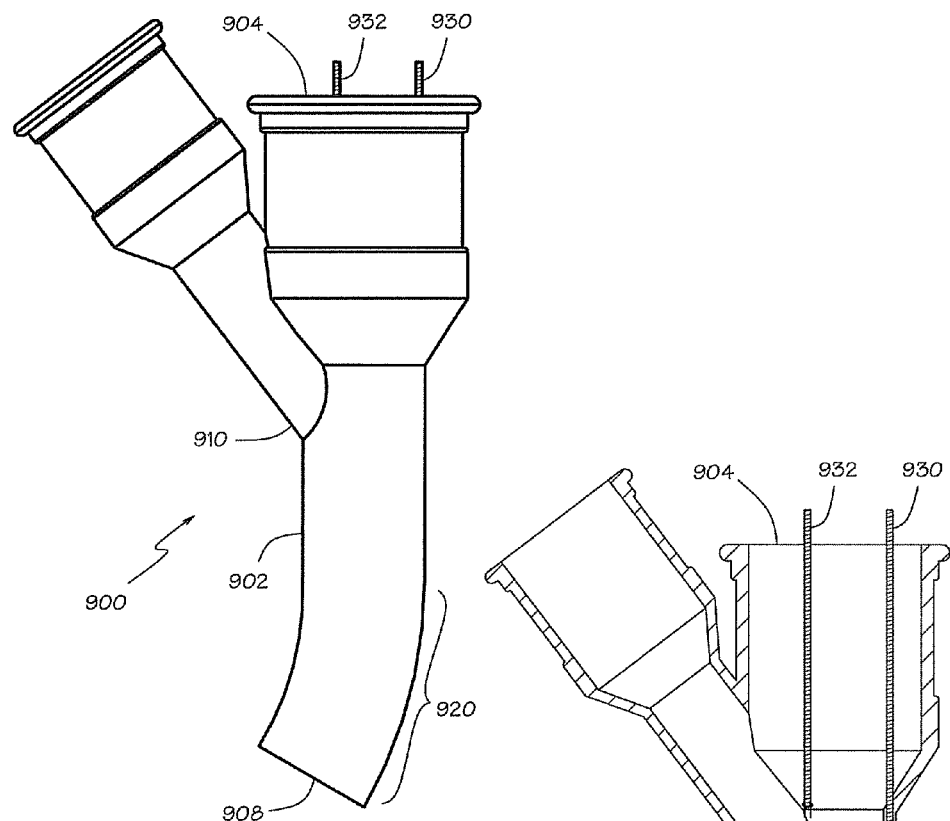
FIG. 9 is a side view of a cannula for use in minimally invasive surgery that includes a flexible section.

FIG. 9 is a side view of a cannula 900 for use in minimally invasive surgery that includes a curved section 920 extending the cannula lumen 902. This cannula 900 would be used with a flexible surgical instrument having a flexible shaft that conforms to the curve of the cannula as the instrument is passed from the proximal end 904 to the distal end 908 through the tubular member or lumen 902. The curved section 920 may be adjustable such that the amount and direction of the curvature can be adjusted, such as by pulling on guide cables 930, 932.

Figure 10:
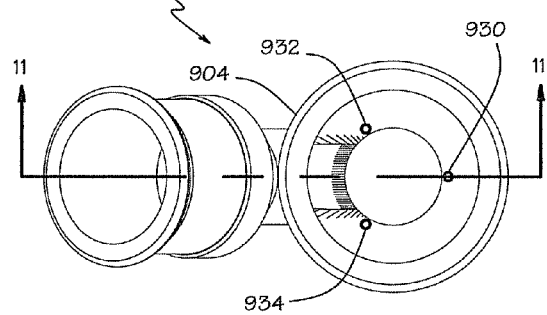
FIG. 10 is a top view of the cannula of FIG. 9.

FIG. 10 is a top view of the cannula of FIG. 9. Guide cables 930, 932, 934 may emerge from the proximal end 904 to be routed to a backend mechanism. The guide cables may be routed through bores in the sidewall of the tubular portion 902 of the cannula 900. As can be seen in the top view, the guide cables 932, 934 are routed to avoid interfering with the service port 910 in the sidewall. In one embodiment the backend mechanism may lock the flexible section 920 in a desired curvature and orientation. In another embodiment the backend mechanism may include robotic actuators that allow robotic control of the shape and orientation of the flexible section 920 of the cannula 900.

Figure 11:
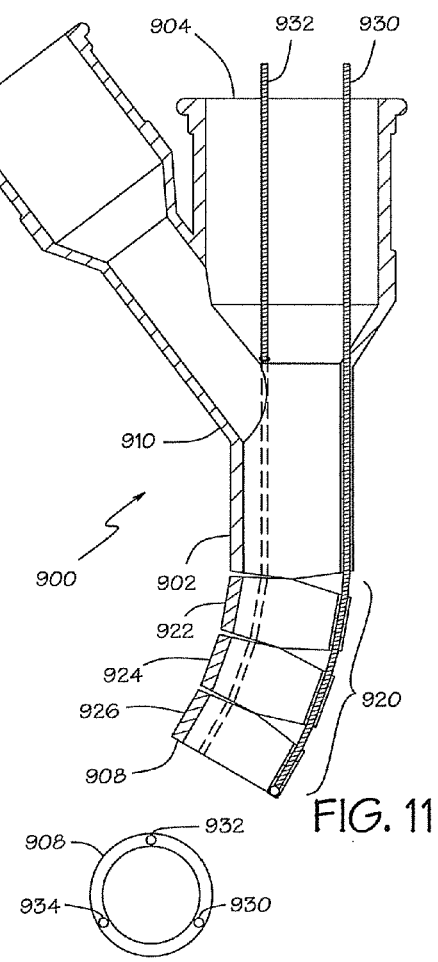
FIG. 11 is cross-section view taken along a line corresponding to the line 11-11 in FIG. 10 showing a construction for the flexible section. including jointed links and cables for locking the flexible section

FIG. 11 is cross-section view taken along a line corresponding to the line 11-11 in FIG. 10 showing a construction for the flexible section 920. The flexible section may include jointed links 922, 924, 926 and cables 930, 932 for locking and/or steering the jointed links. It will be appreciated that if jointed links are used to construct an articulated flexible section 920, a conforming cover (not shown in FIG. 11) may be provided to provide a smooth curved surface on the exterior and/or interior of the cannula.

Figure 12:
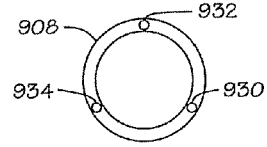
FIG. 12 is a plan view of the distal end of the cannula of FIG. 9.

FIG. 12 is a plan view of the distal end 908 of the cannula 900 of FIG. 9. If guide cables 930, 932, 934 are provided, they may pass through bores in the sidewall of the tubular portion 902 of the cannula 900 or other guide structures and be coupled to the distal end 908, such as by balls crimped onto the ends of the guide cables that engage recesses at the distal end of the bores in the sidewall.

It will be appreciated that the above describe cannulas 100, 800, 900 may be used to service a minimally invasive surgical instrument without removing the surgical instrument from the tubular member 102, 802, 902 in ways other than removing an object grasped by the surgical instrument. For example, objects may be transferred into the cannula and grasped by the surgical instrument to be taken to the surgical site. As an example of an inward transfer, a needle and suture may be transferred through the service port 110, 810, 910 to the surgical instrument 402 by the servicing instrument 400, 830. This may allow the surgeon to quickly grasp it and return to the surgical site under teleoperated control As another example, the surgical instrument may be cleaned by withdrawing the surgical instrument into the tubular member such that an operative end of the surgical instrument is within the central region of the tubular member. A servicing instrument 400, 830 may be introduced through the service port 110, 810, 910 to service the minimally invasive surgical instrument 402 with the servicing instrument in the central region 106, 806 without removing the surgical instrument from the tubular member 102, 802, 902. For example, the image forming end 406 of the camera instrument 404 may be cleaned without removing the camera from the cannula 100, 800, 900 in this way.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A method of positioning surgical instruments used in minimally invasive surgeries, the method comprising:
    positioning a cannula in a patient, the cannula having a proximal opening external to the patient, a distal opening inside the patient, and a service port defined in a sidewall of the cannula, the service port being a second opening external to the patient;
    inserting at least a surgical instrument and a camera instrument into the cannula through the proximal opening of the cannula;
    positioning an end effector of the surgical instrument within the cannula and adjacent the service port, wherein the service port is sized to allow a servicing instrument to be inserted into the cannula to transfer an object between the end effector and a position outside the cannula; and
    positioning the camera instrument to place the end effector positioned within the cannula adjacent the service port and the servicing instrument within a field of view of the camera instrument.

2. The method of claim 1 wherein positioning the end effector of the surgical instrument comprises moving the surgical instrument with an actuator.

3. The method of claim 1 wherein positioning the end effector of the surgical instrument comprises moving the surgical instrument with a servo controlled actuator.

4. The method of claim 1 wherein positioning the camera comprises moving the camera with an actuator.

5. The method of claim 1 wherein positioning the camera comprises moving the camera with a servo controlled actuator.

6. The method of claim 1 wherein positioning the camera comprises positioning an imaging end of the camera within the cannula.

7. The method of claim 1 further comprising displaying an image captured by the camera of the transfer of the object.

8. A robotic system for use in minimally invasive surgery, the system comprising:
- a cannula including a proximal opening, a distal opening, and a service port defined in a sidewall of the cannula, wherein the proximal opening is configured to be placed external to a patient, the distal opening is configured to be placed inside the patient, and the service port is configured to be a second opening external to the patient and is sized to allow a servicing instrument to be inserted into the cannula to transfer an object between a first position inside the cannula and a second position outside the cannula;
- a surgical instrument including an end effector, the surgical instrument being inserted into the cannula through the proximal opening of the cannula;
- a first actuator coupled to the surgical instrument, the first actuator configured to selectively position the end effector within the cannula and adjacent the service port;
- a camera instrument, the camera instrument being inserted into the cannula through the proximal opening of the cannula adjacent the surgical instrument; and
- a second actuator coupled to the camera instrument, the second actuator configured to selectively position the camera instrument at one of a first position to place a surgical site within a field of view of the camera instrument and a second position to place the end effector, when positioned within the cannula adjacent the service port, and the servicing instrument within a field of view of the camera instrument.

9. The robotic system of claim 8 wherein the first actuator is a servo controlled actuator.

10. The robotic system of claim 8 wherein the second actuator is a servo controlled actuator.

11. The robotic system of claim 8 wherein the second actuator is further configured to selectively position the camera instrument within the cannula.

12. The robotic system of claim 8 further comprising a video display configured to display an image captured by the camera of the transfer of the object.

13. The robotic system of claim 8 wherein the cannula includes a flexible section.

14. The robotic system of claim 13 wherein the flexible section is adapted to be locked in a curved configuration by means of cable routed inside an outer shell of the cannula.

15. The robotic system of claim 13 wherein the flexible section is adapted to be robotically controlled to achieve a desired curved configuration.

16. The robotic system of claim 8 wherein the surgical instrument is flexible.

17. The robotic system of claim 8 wherein the camera instrument is flexible.

18. A robotic system for use in minimally invasive surgery, the system comprising:
- a cannula including a proximal opening, a distal opening, and a service port defined in a sidewall of the cannula, wherein the proximal opening is configured to be placed external to a patient and the distal opening is configured to be placed inside the patient, the service port provides a second opening external to the patient that is sized to allow a servicing instrument to be inserted into the cannula to transfer an object between a first position inside the cannula and a second position outside the cannula;
- a surgical instrument including an end effector, the surgical instrument being inserted into the cannula through the proximal opening of the cannula;
- a camera instrument, the camera instrument being inserted into the cannula through the proximal opening of the cannula adjacent the surgical instrument;
- means for positioning an end effector of the surgical instrument within the cannula and adjacent the service port; and
- means for positioning the camera instrument to place the end effector positioned within the cannula adjacent the service port and the servicing instrument within a field of view of the camera instrument.

19. The robotic system of claim 18 wherein the means for positioning the camera is further for positioning the camera within the cannula.

20. The robotic system of claim 18 further comprising means for displaying an image captured by the camera of the transfer of the object.

21. The robotic system of claim 18 further comprising means for providing a curved configuration of the cannula.

* * * * *